(12) United States Patent
Jia et al.

(10) Patent No.: US 9,732,388 B2
(45) Date of Patent: Aug. 15, 2017

(54) NUCLEIC ACID MARKERS FOR RAPID DIAGNOSIS OF KAWASAKI DISEASE AND KIT FOR DETECTION OF THE NUCLEIC ACID MARKERS

(71) Applicant: GUANGZHOU SAGENE BIOTECH CORP., Guangzhou, Guangdong (CN)

(72) Inventors: Hongling Jia, Guangdong (CN); Gong Zhang, Guangdong (CN); Chaowu Liu, Guangdong (CN); Li Zhang, Guangdong (CN); Jie Chen, Guangdong (CN); Hongbin Zeng, Guangdong (CN); Minfei Yu, Guangdong (CN)

(73) Assignee: GUANGZHOU SAGENE BIOTECH CORP., Guangzhou (CN)

( * ) Notice: Subject to any disclaimer, the term of this patent is extended or adjusted under 35 U.S.C. 154(b) by 0 days.

(21) Appl. No.: 15/032,320

(22) PCT Filed: Dec. 26, 2014

(86) PCT No.: PCT/CN2014/095152
§ 371 (c)(1),
(2) Date: Apr. 27, 2016

(87) PCT Pub. No.: WO2016/082272
PCT Pub. Date: Jun. 2, 2016

(65) Prior Publication Data
US 2016/0333408 A1      Nov. 17, 2016

(30) Foreign Application Priority Data
Nov. 27, 2014 (CN) .......................... 2014 1 0709423

(51) Int. Cl.
C07H 21/02       (2006.01)
C07H 21/04       (2006.01)
C12Q 1/68        (2006.01)

(52) U.S. Cl.
CPC ...... *C12Q 1/6883* (2013.01); *C12Q 2600/158* (2013.01); *C12Q 2600/178* (2013.01)

(58) Field of Classification Search
CPC .......................... C12N 2310/11; C12N 15/113
See application file for complete search history.

(56) References Cited

PUBLICATIONS

1st Office Action of counterpart Chinese Patent Application No. 201410709423.0 issued on Feb. 5, 2016.
Zhou, Aihua, The Expression Specifically Related to miRNA in Peripheral Blood Cells of Kawasaki Disease, Proceedings of National Program on the Development of Diagnosis and Treatment of Pediatric Diseases in 2011 Academic Annual Conference of Society of Pediatrics, Zhejiang Medical Association, Jul. 7, 2011, p. 293.
WD Stamer, Protein profile of exosomes from trabecular meshwork cells, J Proteomics, May 16, 2011, pp. 796-804, vol. 74, No. 6.
JM Street, Identification and proteomic profiling of exosomes in human cerebrospinal fluid, Journal of Translational Medicine, Jan. 2012.

*Primary Examiner* — Amy Bowman

(57) ABSTRACT

The present invention provides nucleic acid markers for rapid diagnosis of KD and a kit for detection of the nucleic acid markers. The nucleic acid markers are 4 miRNAs, and the kit comprises primers for quantitative detection of the 4 miRNAs by fluorescent quantitative PCR. The diagnosis of KD can be performed only by quantificationally detecting the contents of the 4 miRNAs in serum exosomes and then analyzing the Ct values of the 4 miRNAs. The present invention possesses the advantages of easily-obtained sample, simple operation, high specificity, time saving, accurate and reliable detection result, etc., so children with KD can be timely and accurately diagnosed. Particularly, KD can be easily distinguished from common virus infection with similar symptoms only by one test. The present invention may play an important role in rapid diagnosis of KD of children and further provide a direction for developing rapid diagnostic kit of KD.

3 Claims, 4 Drawing Sheets

SEQUENCE LISTING

<160> NUMBER OF SEQ ID NOS: 16

<210> SEQ ID NO 1
<211> LENGTH: 19
<212> TYPE: RNA
<213> ORGANISM: homo sapiens

<400> SEQUENCE: 1
aauggauuuu uggagcagg                                                      19

<210> SEQ ID NO 2
<211> LENGTH: 22
<212> TYPE: RNA
<213> ORGANISM: homo sapiens

<400> SEQUENCE: 2
guccacuucu gccugcccug cc                                                  22

<210> SEQ ID NO 3
<211> LENGTH: 22
<212> TYPE: RNA
<213> ORGANISM: homo sapiens

<400> SEQUENCE: 3
uucaccaccu ucuccaccca gc                                                  22

<210> SEQ ID NO 4
<211> LENGTH: 23
<212> TYPE: RNA
<213> ORGANISM: homo sapiens

<400> SEQUENCE: 4
aggaagcccu ggaggggcug gag                                                 23

<210> SEQ ID NO 5
<211> LENGTH: 44
<212> TYPE: DNA
<213> ORGANISM: artificial sequence
<220> FEATURE:
<223> OTHER INFORMATION: synthetic

<400> SEQUENCE: 5
ctcaactggt gtcgtggagt cggcaattca gttgagcctg ctcc                          44

<210> SEQ ID NO 6
<211> LENGTH: 50
<212> TYPE: DNA
<213> ORGANISM: artificial sequence
<220> FEATURE:
<223> OTHER INFORMATION: synthetic

<400> SEQUENCE: 6
gtcgtatcca gtgctgggtc cgagtgattc gcactggata cgacggcagg                    50

<210> SEQ ID NO 7
<211> LENGTH: 44
<212> TYPE: DNA
<213> ORGANISM: artificial sequence
<220> FEATURE:
<223> OTHER INFORMATION: synthetic

<400> SEQUENCE: 7
ctcaactggt gtcgtggagt cggcaattca gttgagagaa gtag                          44

-continued

```
<210> SEQ ID NO 8
<211> LENGTH: 50
<212> TYPE: DNA
<213> ORGANISM: artificial sequence
<220> FEATURE:
<223> OTHER INFORMATION: synthetic

<400> SEQUENCE: 8
gtcgtatcca gtgctgggtc cgagtgattc gcactggata cgacctccag          50

<210> SEQ ID NO 9
<211> LENGTH: 30
<212> TYPE: DNA
<213> ORGANISM: artificial sequence
<220> FEATURE:
<223> OTHER INFORMATION: synthetic

<400> SEQUENCE: 9
acactccagc tgggaatgga tttttggagc                                30

<210> SEQ ID NO 10
<211> LENGTH: 18
<212> TYPE: DNA
<213> ORGANISM: artificial sequence
<220> FEATURE:
<223> OTHER INFORMATION: synthetic

<400> SEQUENCE: 10
ctcaactggt gtcgtgga                                             18

<210> SEQ ID NO 11
<211> LENGTH: 18
<212> TYPE: DNA
<213> ORGANISM: artificial sequence
<220> FEATURE:
<223> OTHER INFORMATION: synthetic

<400> SEQUENCE: 11
agcccgtcca cttctgcc                                             18

<210> SEQ ID NO 12
<211> LENGTH: 19
<212> TYPE: DNA
<213> ORGANISM: artificial sequence
<220> FEATURE:
<223> OTHER INFORMATION: synthetic

<400> SEQUENCE: 12
cagtgctggg tccgagtga                                            19

<210> SEQ ID NO 13
<211> LENGTH: 32
<212> TYPE: DNA
<213> ORGANISM: artificial sequence
<220> FEATURE:
<223> OTHER INFORMATION: synthetic

<400> SEQUENCE: 13
acactccagc tgggttcacc accttctcca cc                             32

<210> SEQ ID NO 14
<211> LENGTH: 18
<212> TYPE: DNA
<213> ORGANISM: artificial sequence
<220> FEATURE:
<223> OTHER INFORMATION: synthetic
```

```
<400> SEQUENCE: 14
ctcaactggt gtcgtgga                                                    18

<210> SEQ ID NO 15
<211> LENGTH: 18
<212> TYPE: DNA
<213> ORGANISM: artificial sequence
<220> FEATURE:
<223> OTHER INFORMATION: synthetic

<400> SEQUENCE: 15
gccgagagga agccctgg                                                    18

<210> SEQ ID NO 16
<211> LENGTH: 19
<212> TYPE: DNA
<213> ORGANISM: artificial sequence
<220> FEATURE:
<223> OTHER INFORMATION: synthetic

<400> SEQUENCE: 16
cagtgctggg tccgagtga                                                   19
```

NUCLEIC ACID MARKERS FOR RAPID DIAGNOSIS OF KAWASAKI DISEASE AND KIT FOR DETECTION OF THE NUCLEIC ACID MARKERS

REFERENCE TO SEQUENCE LISTING

The substitute Sequence Listing is submitted to replace the previously submitted Sequence Listing as an ASCII formatted text filed via EFS-Web, with a file name of "Substitute Sequence Listing v2.TXT", a creation date of May 11, 2016, and a size of 2,482 bytes. The substitute Sequence Listing filed via EFS-Web is part of the specification and is incorporated in its entirety by reference herein.

FIELD OF THE INVENTION

The present invention relates to nucleic acid markers for rapid diagnosis of kawasaki disease and a kit for detection of the nucleic acid markers.

BACKGROUND OF THE INVENTION

Kawasaki disease (KD) is an acute febrile vasculitis syndrome which occurs throughout the body, and the etiology of kawasaki disease remains unknown. The disease was first discovered by a Japanese scholar Tomisaku Kawasaki in Japan in 1961, and was first reported in 1967. Since 1970, kawasaki disease has been successively reported in almost all countries and regions in the world, and the highest incidence is in Asian. Recently, KD often occurs in children under five years of age. KD is characterized by fever, mucositis, rash, cervical lymphadenopathy and changes in the extremities. The pathological features of KD mainly include systemic vasculitis involving small- and medium-sized artery vascular, especially, KD can cause inflammatory injury in coronary arteries, which would lead to thrombotic infarction, stenosis, ectasia and aneurysms. Giant coronary aneurysm may occur in some children patient, and the long-standing giant coronary aneurysm can cause coronary artery stenosis or occlusion in the later stage, which may lead to ischemic heart disease and even death. In addition, KD can also lead to myocardial hypertrophy, focal myocardial ischemia, myocardial fibrosis, myocardial infarction in adulthood, and even sudden death in severe cases. Even KD patients with coronary artery aneurysms timely receive targeted and effective treatment, some patients will still die due to giant coronary artery aneurysms. The incidence rate of coronary artery ectasia has been reported to be 18.6-26.0%, and the incidence rate of coronary artery aneurysms has been reported to be 3.1%-5.2%. What's more, the incidence rate of coronary artery aneurysms has been reported to be on the rise year by year. Coronary artery aneurysm is the most serious complication of KD. When coronary artery aneurysm occurs, the patient is at high risk for developing vascular intima thrombus and hyperplasia, which may result in stenosis adjacent to the lumen of coronary artery. The retaining blood in the aneurysm is at high risk for developing thrombus, which will reduce blood flow to the region adjacent to the coronary artery aneurysm and cause myocardial infarction and sudden death. When the diameter of the aneurysm is ≥8 mm, the aneurysm are classified into giant aneurysm, its regression will be more difficult, and the incidence rate of stenosis will significantly increase as time goes on. In a word, KD puts children patient at high risk and brings serious impact on their lives. At present, the treatment methods for coronary artery aneurysms caused by KD include long-term anticoagulant therapy, thrombolytic therapy, coronary artery bypass surgery, heart transplantation and interventional therapy. However, all of these methods are remedial therapies, and the results are usually not satisfactory. The cost of treatment is considerably high, and quality of life in treated children can't be guaranteed.

It has been reported that in developed countries or regions, such as Japan and the United States, the coronary complication caused by KD has replaced rheumatic fever as the most common cause of acquired heart disease in children, and is one of dominant factors for ischemic heart disease in late adulthood. In China, the incidence rate of KD is also high, next only to Japan and South Korea, and has already replaced rheumatic fever as the most common cause of acquired heart disease in children. What' more, its incidence in China is increasing in recent years, which poses a potential health risk to children's heart and vascular and great economic burden to society.

At present, KD can be diagnosed by clinical symptoms, ultrasound imaging and laboratory tests. The clinical diagnosis of KD is mainly based on clinical symptoms, however, children are often not diagnosed until they have been found several typical clinical symptoms and other illnesses with similar symptoms have been ruled out. Therefore, the timeliness of clinical diagnosis is poor. For ultrasound imaging method, the pathological changes in coronary artery are determined by echocardiography images, however, the ultrasound imaging method has its limitation for diagnosis of early or minor coronary artery disease in children with KD. For laboratory tests, the systemic inflammatory indexes are used to facilitate the diagnosis of KD in children, including increased peripheral blood leukocytes and neutrophils in the acute phase, mild anemia, increased platelets, significantly increased C-reactive protein, and significantly increased rythrocyte sedimentation rate, etc. The inflammatory indexes can only be seen as assisted or indirect diagnosis references, so the specificity and pertinence of the laboratory tests are not ideal. What's more, many other diseases, especially infectious diseases, may also cause systemic inflammation, so the common diagnostic methods often result in confusions with other infectious diseases, which then lead to delayed treatment.

At present, the clinical diagnosis of atypical KD is relatively difficult. The incidence rate of atypical KD is approximately 10%-36%, and is increasing year by year. The clinical symptoms of atypical KD are also diverse and complex, and it is more likely to be misdiagnosed as respiratory tract infection, sepsis, drug rash, scarlet fever, measles, lymph node inflammation, juvenile rheumatoid and other diseases. Patients often miss optimal timing for treatment due to misdiagnosis or missed diagnosis. As a result, coronary artery injuries have already occurred in many children when they are definitely diagnosed with KD.

Recently, scholars have been working hard to find markers for early diagnosis of KD. However, since the etiology and pathogenesis of KD remain unknown, most scholars focus on genes, cytokines, and inflammatory cytokines, the biomarkers that have been found can't be used as specific markers for diagnosis of KD. Although it has been reported that some proteins and genes, such as heart-type fatty acid binding protein (h-FABP), matrix metalloproteinase-9 (MMP-9), and N-terminal B-type natriuretic peptide (NT-pro BNP), could be used as molecular markers for diagnosis of KD, the molecular markers are unable to satisfy both sensitivity and specificity, and are more likely to cause detection error resulting from sampling methods and operating procedure, etc., thus, the molecular markers have not been confirmed by large-scale clinical trials. To date, there is no universally recognized marker and methods for diagnosis of KD. Therefore, it is important to find a molecular marker for rapid and accurate diagnosis of kawasaki disease, which is useful for the clinical treatment of KD so as to avoid occurrence of coronary artery disease, improve prognosis and quality of life in treated children.

Exosomes are cell-secreted vesicles derived from late endosomes (also known as multivesicular endosomes). The internal vesicles are released into the extracellular space when the multivesicular endosomes fuse with the plasma membrane. It has been reported that exosomes derived from different cells contain key functional molecular constituents of their cells of origin. The reported diameter of exosomes is between 30 and 100 nm. Exosomes are present in many cells, and contain various molecular constituents, including proteins, lipids and micro RNAs. The exosomal proteins and microRNAs vary with the cells and tissues of origin, as well as the biological function of the exosomes. Exosomes in blood are solid components with low density and are reported to contain a great deal of biomarker information, thus exosomes have attracted widespread attention in recent years. In human body fluids (such as serum, urine, tissue fluid), RNAs wrapped in exosomes will not be degraded by nuclease, and will not be affected by highly expressed proteins (such as albumin, IgG). The constituents contained in exosomes, which are part of constituents of their cells of origin, give a possibility to detect changes in certain proteins and nucleic acids in the cell. In recent years, increased attention has been paid to the role that exosomes in body fluids may play in clinical diagnosis. For example, micro RNAs present in serum of cancer patients can be used as molecular markers for early diagnosis of several types of cancers. In addition, OMICS provides an optimal platform and technique to detect specific molecular markers for diseases of unknown etiology. OMICS informally refers to a field of genomics, proteomics, transcriptomics, etc., OMICS aims at the collective characterization and quantification of all DNA, RNA or proteins in samples by certain experiments and data analysis. It is expected to detect disease-specific molecular markers by comparing data from normal individual and data from patient, and the molecular markers may play an important role in early diagnosis, etiological analysis, in-depth study and treatment of disease, etc. Currently, these methods have been widely used in the studies of cell proliferation, differentiation, abnormal transformation, tumor formation and other aspects, involving liver cancer, breast cancer, colon cancer, bladder cancer, prostate cancer, lung cancer, kidney cancer, neuroblastoma, etc. A series of tumor-associated proteins have been identified, which is helpful for early diagnosis of tumor, detection of drug targets, therapeutic evaluation and prognosis. Some nucleic acid molecules can also be used as molecular markers for diagnosis of diseases. The nucleic acid markers have high sensitivity and good specificity in clinical diagnosis, and can be accurately quantified, thus they are especially suitable as early diagnostic markers.

Mature microRNA (miRNA) is a small non-coding RNA molecule with sizes of 17-25 nucleotides. MicroRNA inhibits the translation of target mRNA via base-pairing with complementary sequences within 3'-UTR, 5'-UTR and encoding region of target mRNA, that is to say, miRNA functions in post-transcriptional regulation of target gene expression. Bioinformatics studies show that each miRNA can regulate multiple target genes, whereas one target gene can also be regulated by multiple miRNAs. According to conservative estimates, miRNAs appear to target about 60-70% of human protein encoding genes. A single miRNA may bind with hundreds of target mRNAs with different functions, so as to play regulatory roles. MicroRNAs involve in almost all physiological and pathological processes in mammalian, such as ontogenesis, tissue differentiation, apoptosis and energy metabolism, thus miRNAs are associated with occurrence and development of various diseases.

The previous studies on miRNAs mainly focus on their actions in cells. In 2008, Mitchell et al. constructed a small RNA library by isolating RNAs with sizes of 18-24 nucleotides from plasma of healthy people, 125 DNA clones obtained were sequenced and analyzed, and 37 miRNA molecules in the plasma samples were cloned, including let-7a, miR-16, miR-15b, etc. It is found that miRNAs can exist in human plasma in a stable form, which prevents miRNAs from degradation by endogenous RNase. During the same time period, Chen et al. analyzed miRNAs in serum by high-throughput sequencing technology, and more than 100 and 91 miRNAs were detected in serum of healthy male and female people, respectively. It is found that these miRNAs remain stable even under extreme conditions (such as high temperature, extremely low or high pH, and multiple freeze-thaw), while most other RNAs have been degraded. In addition, according to the detection results of miRNAs in serum/plasma of healthy people and patients, miRNAs are found to widely exist in serum/plasma of healthy people and patient, and their expression profiles specifically vary with physiological status, disease types and disease degrees. Recent research shows that different tumors have specific miRNA profiles, and tumor-derived miRNAs can be released into circulatory system and blood tissue. MicroRNAs in blood can't be degraded by RNase and thus are quite stable. Therefore, miRNAs in serum or plasma have potential as cancer biomarker. For example, recent research finds that the expression level of miR-21 in serum of patients with diffuse large B-cell lymphoma is higher than that in serum of healthy people. Since there are plenty of stable microRNAs in human serum or plasma, and exosomes in blood are reported to carry abundant biomarkers information, and exosomes derived from different cells contain key functional moleculars of their cells of origin, increased attention has been paid to the role that exosomes in body fluids may play in clinical diagnosis. For example, microRNA molecular markers in the serum of cancer patient have been used for early diagnosis of various cancers. Based on the above phenomena, we could detect exosomal microRNAs whose expression levels change obviously in the serum of patient with KD, and then use these exosomal microRNAs as biomarkers for early diagnosis of KD.

SUMMARY OF THE INVENTION

An aim of the present invention is to provide nucleic acid markers for rapid diagnosis of kawasaki disease.

Another aim of the present invention is to provide a kit for rapid diagnosis of kawasaki disease.

The technical solutions of the present invention are as follows:

Use of a combination of small molecule RNAs consisting of miR-1246, miR-4436b-5p, miR-197-3p and miR-671-5p as a biomarker set for rapid diagnosis of kawasaki disease.

Preferably, the small molecule RNAs consisting of miR-1246, miR-4436b-5p, miR-197-3p and miR-671-5p are miR-1246, miR-4436b-5p, miR-197-3p and miR-671-5p in serum exosomes.

A kit for rapid diagnosis of kawasaki disease comprises reagents for quantitative detection of the expression of miR-1246, miR-4436b-5p, miR-197-3p and miR-671-5p in serum exosomes.

Preferably, the kit comprises primers as set forth in SEQ ID NOs: 9-16 for the detection of miR-1246, miR-4436b-5p, miR-197-3p and miR-671-5p by fluorescence-based quantitative PCR.

Preferably, the kit comprises primers as set forth in SEQ ID NOs: 5-8 for reverse transcription of miR-1246, miR-4436b-5p, miR-197-3p and miR-671-5p.

The technical advantage of the present invention are as follows:

1) Compared with the traditional methods for diagnosis of kawasaki disease (such as clinical symptoms, ultrasound imaging, laboratory tests, etc.), the present invention possesses the advantages of easily-obtained sample, simple operation, high specificity, time saving, accurate and reliable detection result, etc. Children with kawasaki disease can be timely and accurately diagnosed according to the present invention. Particularly, kawasaki disease can be easily distinguished from common virus infection with similar symptoms only by one test. Thus, the present invention has significant advantages compared with traditional methods for diagnosis of kawasaki disease, which can play an important role in rapid diagnosis of kawasaki disease of children and further provide possibility for developing rapid diagnostic kit of kawasaki disease.

2) The present invention focuses on detecting stable miRNAs in the plasma/serum, while the traditional molecular diagnostic methods focus on detecting proteins. In quantitative aspect, the accuracy and sensitivity for detection of miRNAs are considerably high, even a single miRNA molecule can be detected by qPCR, while the accuracy and sensitivity for detection of protein are low.

3) The traditional molecular diagnostic methods are based on detecting the absolute content of certain proteins, and then comparing the obtained data with reference range or standard sample so as to obtain the result. However, the absolute content may vary with sampling process, extraction efficiency, operating procedure of the operator, etc., which will result in errors in the detection result. The present invention detects several miRNAs rather than a single miRNA, thus the reliability of the result is much higher. In addition, the present invention uses several miRNAs in the sample as cross-references, which can completely avoid errors in the detection result caused by sampling process, extraction efficiency, operating procedure of the operator, etc., thus the present invention has higher stability than traditional methods and has the potential to facilitate low-cost and large-scale application.

BRIEF DESCRIPTION OF THE DRAWINGS

FIGS. 1A, 1B and 1C show the characteristics of serum exosomes of healthy children (control) and children with KD, wherein FIG. 1A shows the morphological characteristics of serum exosomes of healthy children and children with KD under transmission electron microscope; FIG. 1B shows the diameter distribution ranges of 200 serum exosomes of healthy children and children with KD under scanning electron microscopy; FIG. 1C shows the relative contents (western blot) of three exosome protein markers CD9, CD81 and TSG101 in exosomes (Ex) and serum (S).

FIGS. 3A, 3B and 3C show the t-test results obtained by further verifying the results of microRNA Microarray of serum exosomes of 5 children infected by syncytial virus, 5 children infected by adenovirus, 20 children with KD and 20 healthy children by fluorescence quantitative PCR and comparing one to another, wherein FIG. 3A shows the comparison result of KD group and healthy group; FIG. 3B shows the comparison result of healthy group and syncytial virus (RSV) group; FIG. 3C shows the comparison result of healthy group and adenovirus (ADV) group.

DETAILED DESCRIPTION OF ILLUSTRATED EMBODIMENTS

For the purpose of promoting an understanding of the technical solution of the present invention, the present invention will be explained in detail referring to the attached drawings and embodiments. Although the invention has been described and illustrated with reference to the specific embodiments, it is not intended that the invention be limited to those illustrative embodiments. If some experimental conditions are not specified in the following embodiments, they are generally performed according to common conditions, such as the experimental conditions described in "molecular cloning: a laboratory manual (Sambrook et al, New York: Cold Spring Harbor Laboratory Press, 1989)" or recommended by manufacturer. All the chemical reagents used in the embodiments are commercially available.

In the present invention, both the difference between the expression level of miR-1246 and miR-4436b-5p and the difference between the expression level of miR-197-3p and miR-671-5p in serum exosomes of children with KD are significantly different with that in serum exosomes of healthy children. What's more, the larger the sample size, the more obvious the trend is. In addition, the most prominent symptom of kawasaki disease is persistent fever, and the body temperature exceeds 39° C., in order to distinguish kawasaki disease from other febrile diseases, the two pairs of miRNAs in children with other febrile diseases (infected by syncytial virus, adenovirus virus, and EB virus) are also detected. The experimental results show that the expression level of the two pairs of miRNAs in children with KD and children with other febrile diseases can be clearly separated, that is to say, the two pairs of miRNAs (miR-1246 and miR-4436b-5p; miR-197-3p and miR-671-5p) can be used as specific molecular markers for kawasaki disease. Children with KD can be rapidly diagnosed and distinguished from children with other febrile diseases by analyzing the differences between Ct(miR-1246) and Ct(miR-4436b-5p) and the differences between Ct(miR-197-3p) and Ct(miR-671-5p) in serum exosomes, which may play an important role in early diagnosis of KD.

K. L: Protein profile of exosomes from trabecular meshwork cells. J Proteomics 2011, 74 (6): 796-804 and Street J M, Barran P E, Mackay C L, Weidt S, Balmforth C, Walsh T S, Chalmers R T, Webb D J, Dear J W: Identification and proteomic profiling of exosomes in human cerebrospinal fluid. J Transl Med 2012, 5; 10:5. doi: 10.1186/1479-5876-10-5).

(4) RNA in exosomes was extracted by Trizol reagents (Life Tech Inc, USA), then the concentration and purity of the obtained RNA were measured.

Figure 2:
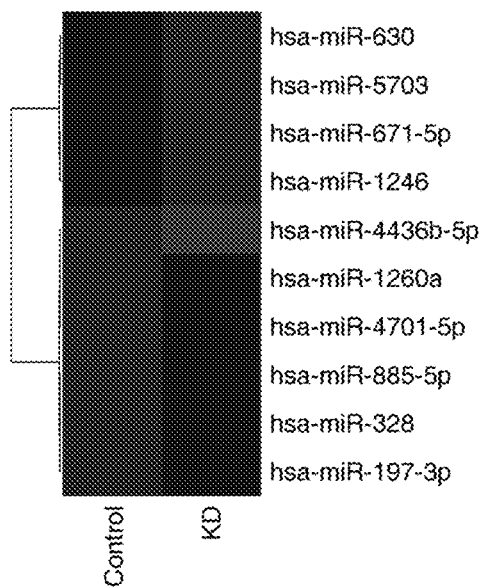
FIG. 2 shows the analysis results of microRNA Microarray of exosomes isolated from the equivalent volume of mixed serum of 5 healthy children and mixed serum of 5 children with KD, only miRNAs whose expression levels up-regulate or down-regulate more than 200 times are listed, wherein KD represents children with KD, control represents healthy children.

(5) The nucleic acid markers were preliminary screened by the following steps: analyzing RNA in exosomes isolated from the equivalent volume of mixed serum of 5 healthy children and mixed serum of 5 children with KD by microRNA Microarray; screening out the miRNAs whose expression levels up-regulate or down-regulate more than 200 times. The miRNAs significantly up-regulated or down-regulated in microRNA Microarray analysis (more than 200 times) include miR-1246, miR-4436b-5p, miR-197-3p and miR-671-5p (see FIG. 2). The nucleic acid sequences of the 4 miRNAs are shown in table 1.

TABLE 1

Nucleic acid sequences of miR-671-5p, miR-4436b-5p, miR-197-3p and miR-1246

| miRNA | miRNA sequences | Accession number |
| --- | --- | --- |
| miR-1246 | aauggauuuuuggagcagg (SEQ ID NO: 1) | MIMAT0005898 |
| miR-44366-5p | guccacuucugccugcccugcc (SEQ ID NO: 2) | MIMAT0019940 |
| miR-197-3p | uucaccaccuucuccacccagc (SEQ ID NO: 3) | MIMAT0000227 |
| miR-671-5p | aggaagcccuggaggggcuggag (SEQ ID NO: 4) | MIMAT0003880 |

EXAMPLE 1

Screening the Nucleic Acid Markers for Rapid Diagnosis of Kawasaki Disease

I. Preliminary Screening (1) 500 μL blood was collected from healthy children and children with KD, respectively, and stored in refrigerator (4° C.) for 1-2 h, then centrifuged at 2000 rpm for 5 minutes, the serum was then isolated and obtained.

(2) Exosomes were extracted from serum according to the instruction of the exosome extraction kit (System Biosciences Inc, Mountain View, Calif.).

Figure 1A:
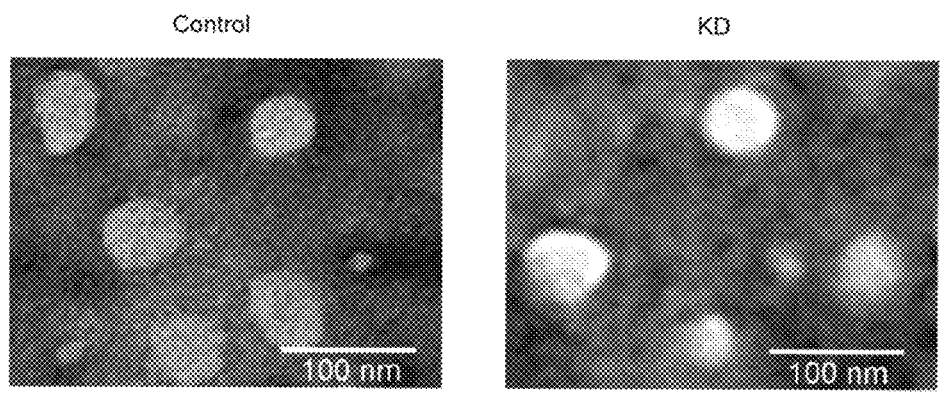
Figure 1B:
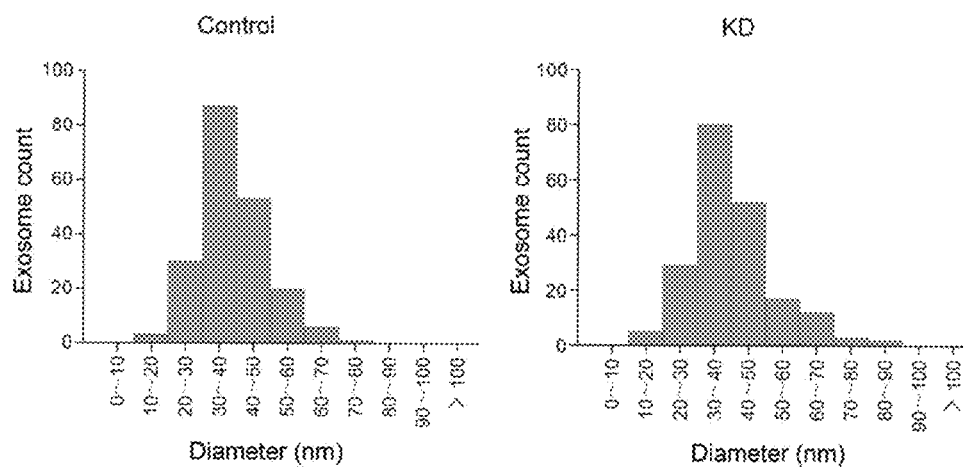
Figure 1C:
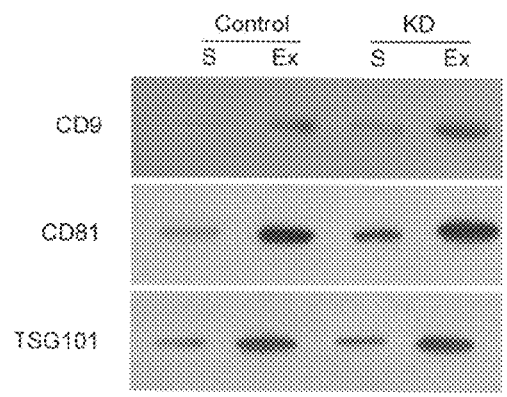

(3) The morphology of the obtained exosomes was observed under transmission electron microscope, and the diameters of all exosomes were determined about 30-100 nm (see FIG. 1A and FIG. 1B). Further, western blot was used to detect the expression level of three exosome protein markers (CD9, CD81 and TSG101) (see FIG. 1C) (refer to Stamer W D, Hoffman E A, Luther J M, Hachey D L, Schey II. Re-screening The nucleic acid markers were re-screened by the following steps: randomly collecting serum of 5 children infected by respiratory syncytial virus (RSV), 5 children infected by adenovirus (ADV), 20 children with KD and 20 healthy children; extracting exosomes in the obtained serum; and detecting the miRNAs screened out in above preliminary screening process by fluorescence quantitative PCR.

Specifically, the cDNA was obtained by reverse transcription, and then fluorescence quantitative PCR was performed, the detailed steps were as follows:

(1) Obtaining cDNA by Reverse Transcription

1) RNA extracted from the exosomes was used as template, and 1.0 μg RNA template was added into a PCR tube free of RNase, then water free of RNA was added into the PCR tube until the total volume was up to 8 μL.

2) The solution was well-mixed, and incubated for 5 min at 85° C. to unfold RNA secondary structure, then immediately placed on ice to prevent the recovery of RNA secondary structure.

3) In the reverse transcription process, the specific reverse transcription primers for the miRNAs screened out in above preliminary screening process are shown in Table 2 (only the primers for miR-1246, miR-197-3p, miR-4436b-5p, and miR-671-5p are listed, the others are not given).

TABLE 2 specific reverse transcription primers for miR-1246,
miR-4436b-5p, miR-197-3p and miR-671-5p

| miRNA | name of primer | sequence of reverse transcription primer |
|---|---|---|
| miR-1246 | miR-1246-RT | CTCAACTGGTGTCGTGGAGTCGGCAATTCAGT TGAGCCTGCTCC (SEQ ID NO: 5) |
| miR-4436b-5p | miR-4436b-5p-RT | GTCGTATCCAGTGCTGGGTCCGAGTGATTCGC ACTGGATACGACGGCAGG (SEQ ID NO: 6) |
| miR-197-3p | miR-197-3p-RT | CTCAACTGGTGTCGTGGAGTCGGCAATTCAGT TGAGAGAAGTAG (SEQ ID NO: 7) |
| miR-671-5p | miR-671-5p-RT | GTCGTATCCAGTGCTGGGTCCGAGTGATTCGC ACTGGATACGACCTCCAG (SEQ ID NO: 8) | the following solution was prepared in another PCR tube free of RNase:

| | |
|---|---|
| 10 mM dNTP (promega) | 2.0 μL |
| RNase inhibitor (promega) | 0.5 μL |
| miR-1246-RT | 0.5 μL |
| miR-4436b-5p-RT | 0.5 μL |
| miR-197-3p-RT | 0.5 μL |
| miR-671-5p-RT | 0.5 μL |
| 5x buffer | 4 μL |
| M-MLV (promega) | 0.5 μL |
| Total volume | 9 μL |

4) The solution of step 3) was added into the solution of step 1), mixed, then incubated for 60 min at 42° C.

5) after incubation for 10 min at 85° C. to inactivate the reverse transcriptase, cDNA was obtained.

(2) Fluorescence Quantitative PCR

During fluorescence quantitative PCR, the fluorescence quantitative PCR primers for the miRNAs screened out in above preliminary screening process are shown in Table 3 (only the primers for miR-1246, miR-197-3p, miR-4436b-5p, and miR-671-5p are listed, the others are not given).

TABLE 3

Fluorescence quantitative PCR primers for miR-1246,
miR-4436b-5p, miR-197-3p and miR-671-5p

| miRNA | name of primer | sequence of fluorescence quantitative PCR primer |
|---|---|---|
| miR-1246 | miR-1246-F | ACACTCCAGCTGGGAATGGATTTTTGGAGC (SEQ ID NO: 9) |
| | miR-1246-R | CTCAACTGGTGTCGTGGA (SEQ ID NO: 10) |
| miR-4436b-5p | miR-4436b-5p-F | AGCCCGTCCACTTCTGCC (SEQ ID NO: 11) |
| | miR-4436b-5p-R | CAGTGCTGGGTCCGAGTGA (SEQ ID NO: 12) |
| miR-197-3p | miR-197-3p-F | ACACTCCAGCTGGGTTCACCACCTTCTCCACC (SEQ ID NO: 13) |
| | miR-197-3p-R | CTCAACTGGTGTCGTGGA (SEQ ID NO: 14) |
| miR-671-5p | miR-671-5p-F | GCCGAGAGGAAGCCCTGG (SEQ ID NO: 15) |
| | miR-671-5p-R | CAGTGCTGGGTCCGAGTGA (SEQ ID NO: 16) |

1) Fluorescence quantitative PCR for the miRNAs screened out in above preliminary screening process was respectively performed according to the following reaction system:

| | |
|---|---|
| cDNA (1:20) | 5.0 μL |
| Upstream primer | 0.5 μL |
| Downstream primer | 0.5 μL |
| 2x SYBR Green qPCR SuperMix | 10 μL |
| ddH2O | 4.0 μL |
| Total volume | 20 μL |

2) The reaction condition of fluorescence quantitative PCR was as follows: 50° C. 2 min; 95° C. 2 min; 95° C. 15 s; 60° C. 32 s; 40 cycles; dissociation curve analysis: temperature 60° C.~95° C.

Figure 3A:
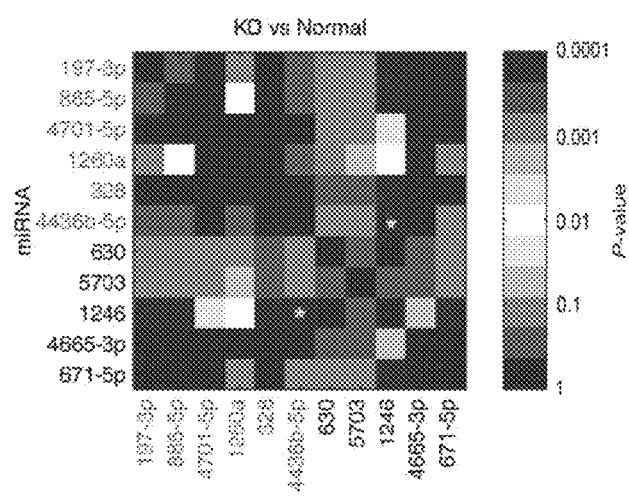
Figure 3B:
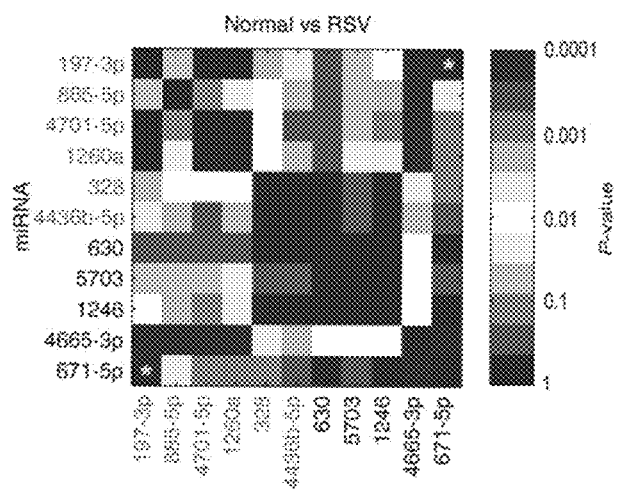

The Ct values of the miRNAs screened out in above preliminary screening process were compared with each other and used as cross-reference so as to avoid bias caused by sampling process, operating procedure etc. After comparing one to another, it is found that the difference between Ct(miR-1246) and Ct(miR-4436b-5p) in KD group is obviously different from that in healthy group ($P<0.01$) (see FIG. 3A); while there are no significant difference in the differences between Ct(miR-1246) and Ct(miR-4436b-5p) in healthy group and other febrile diseases groups, for example, in healthy group and syncytial virus group (RSV) (see FIG. 3B), in healthy group and adenovirus group (ADV) (see FIG. 3C). There is also certain difference in the difference between Ct(miR-1246) and Ct (miR-328), however, the difference between Ct(miR-1246) and Ct (miR-328) are smaller than the difference between Ct(miR-1246)-

Ct(miR-4436b-5p), and the P value of which is higher, so the difference between Ct(miR-1246) and Ct (miR-328) is not adopted.

Figure 3C:
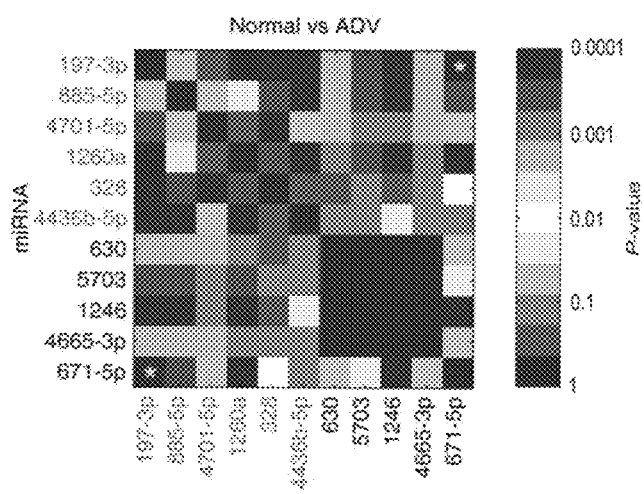

In addition, after comparing one to another, it is found that there are no significant difference in the differences between Ct(miR-197-3p) and Ct (miR-671-5p) in healthy group and KD group (see FIG. 3A); while there are significant difference in the differences between Ct(miR-197-3p) and Ct (miR-671-5p) in healthy group and other febrile diseases groups (P<0.01), for example, in healthy group and syncytial virus group (RSV) (see FIG. 3B), in healthy group and adenovirus group (ADV) (see FIG. 3C).

From the above, the difference between Ct(miR-1246) and Ct(miR-4436b-5p) and the difference between Ct(miR-197-3p) and Ct(miR-671-5p) can be simultaneously used as markers for diagnosis of kawasaki disease, which can improve stability and accuracy for diagnosis of kawasaki disease (especially for early diagnosis of kawasaki disease).

EXAMPLE 2

Verifying the Nucleic Acid Markers for Rapid Diagnosis of Kawasaki Disease

In order to further verify whether the 4 miRNAs (miR-328, miR-197-3p, miR-1246, and miR-671-5p) screened out by example 1 are closely related to rapid and accurate diagnosis of KD, RNAs in exosomes of fresh serum from 30 healthy children, 30 children with KD, 8 children infected by respiratory syncytial virus (RSV), 2 children infected by adenovirus (ADV), 2 children infected by EB virus were extracted, respectively; the obtained exosomal RNAs were then detected by fluorescence quantitative PCR as described in example 1; and the Ct values of miR-1246, miR-328, miR-197-3p and miR-671-5p were measured; the Ct values were then compared with each other and used as cross-reference so as to avoid bias caused by sampling process, operating procedure etc; the difference between Ct(miR-1246) and Ct(miR-4436b-5p) and
the difference between Ct(miR-197-3p) and Ct(miR-671-5p) were calculated; finally, the two differences were used as coordinate axis X and coordinate axis Y to draw a graph.

Figure 4:
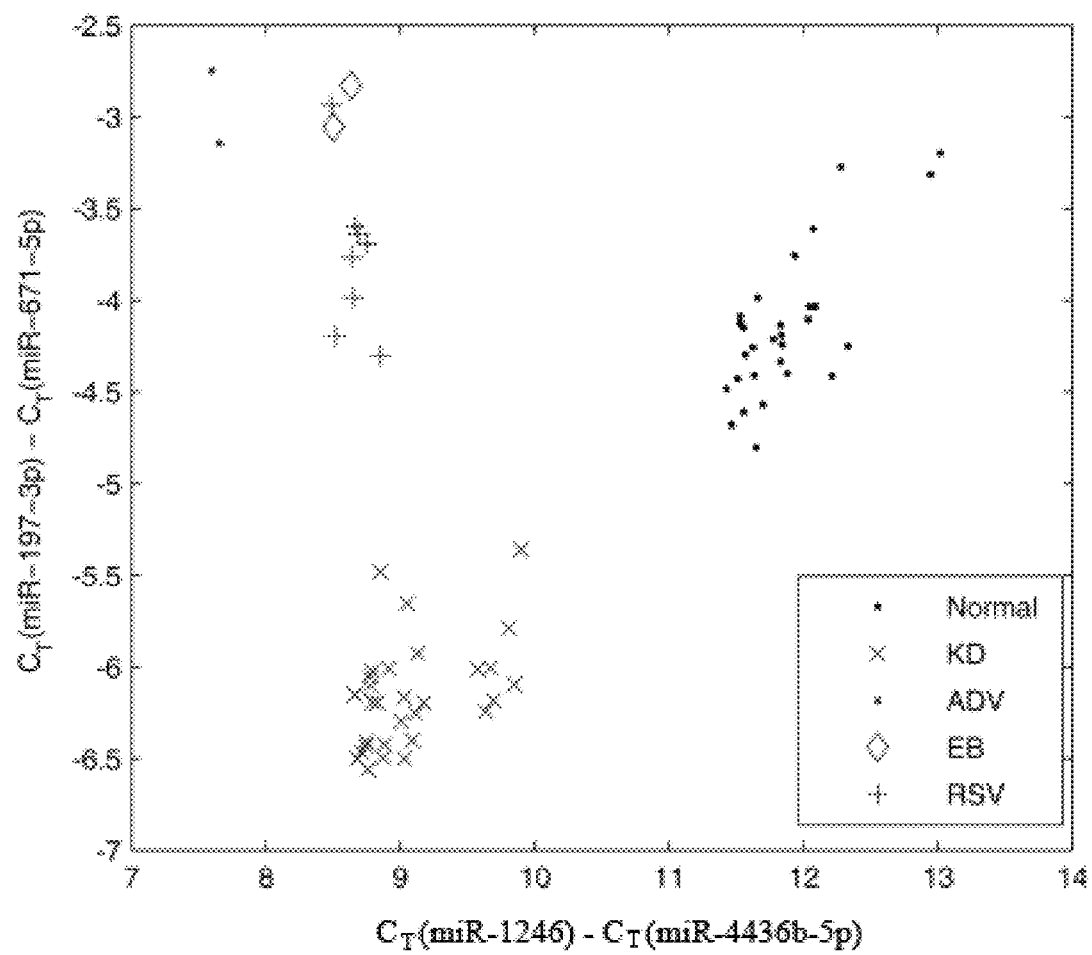
FIG. 4 shows the results obtained by detecting the contents of 4 microRNAs in serum exosomes of 8 children infected by syncytial virus, 2 children infected by EB virus, 2 children infected by adenovirus, 30 children with KD and 30 healthy children by fluorescence quantitative PCR and using the difference between Ct(miR-1246) and Ct(miR-4436b-5p) and the difference between Ct(miR-197-3p) and Ct(miR-671-5p) as two coordinate axises for two-dimensional drawing, respectively, wherein the black dots represent the data from healthy children, the red crosses represent the data from children with KD, and the blue marks represent the data from children infected by various virus.

As shown in FIG. 4, the healthy group (black dots), KD group (x) and febrile diseases groups ("◇" for EB, "+" for RSV, blue dots for ADV) can be exactly distinguished. Based on the sample statistics, the tentative conclusions as follows can be obtained:

define x=Ct (miR-1246)-Ct (miR-4436b-5p), y=Ct (miR-197-3p)-Ct (miR-671-5p);
(1) if y≤−4.9 and y≤−x+5.6, the subject can be diagnosed with kawasaki disease;
(2) if y>−4.9 and x≤10.2, the subject can be diagnosed with virus infection;
(3) if x>10.2 and y>−x+5.6, the subject is normal.

In conclusion, the miR-1246, miR-4436b-5p, miR-197-3p and miR-671-5p in serum exosomes can be used as molecular markers for rapid diagnosis of kawasaki disease. Based on this, a kit for rapid diagnosis of kawasaki disease can also be prepared, and the kit comprises reagents for quantitative detection of miR-1246, miR-4436b-5p, miR-197-3p and miR-671-5p in serum exosomes, for example, the kit comprises primers set forth in SEQ ID NO: 9-16 for detection of miR-1246, miR-4436b-5p, miR-197-3p and miR-671-5p by fluorescent quantitative PCR, and also comprises primers set forth in SEQ ID NO: 5~8 for reverse transcription of the 4 miRNAs.

EXAMPLE 3

Detecting Clinical Samples

Another 80 clinical serum samples were used to verify the rapid diagnosis of kawasaki disease, the specific steps were as follows:
1) extracting RNAs in serum exosomes as described in example 1;
2) treating the obtained RNAs with reverse transcription, and performing quantitative detection of miR-1246, miR-4436b-5p, miR-197-3p and miR-671-5p in exosomes as described in example 1 to obtain the Ct values of the 4 miRNA, then comparing the Ct values of each sample with each other, wherein the Ct values were also used as cross-reference so as to avoid bias caused by sampling process, operating procedure etc;
3) calculating the values of x, y for each sample, wherein x=Ct(miR-1246)−Ct(miR-4436b-5p), y=Ct(miR-197-3p)−Ct(miR-671-5p).
4) analyzing the results, wherein
(1) If y≤−4.9 and y≤−x+5.6, it is KD.
(2) If y>−4.9 and x≤10.2, it is virus infection;
(3) If x>10.2 and y>−x+5.6, it is normal.

According to the above analysis, there were 35 normal samples without KD or virus infection, 28 samples with KD, and 17 samples with virus infection in the 80 samples tested. The detection results of the present invention coincided well with clinical diagnosis made by clinical symptoms, ultrasonic imaging and laboratory tests, etc. Therefore, it can be seen that the present invention has high accuracy.

Compared with current clinical methods for diagnosis of kawasaki disease, molecular markers miR-1246, miR-4436b-5p, miR-197-3p and miR-671-5p for rapid diagnosis of kawasaki disease in children provided in the present invention have taken the advantages of easily-obtained sample, simple operation, high specificity, etc. Especially, the present invention uses several miRNAs in the sample as cross-reference, no reference standard is needed, thus the present invention can completely avoid bias caused by extraction efficiency, operating procedure, etc, it has the potential for clinical application. Further, a kit for quantitative detection of miR-1246, miR-4436b-5p, miR-197-3p and miR-671-5p can also be prepared to diagnose kawasaki disease. Only one test is needed to distinguish KD patients from healthy people and patients infected by febrile virus, the kit can not only be used to distinguish KD patients from healthy people, but it can also be used to eliminate interference caused by other febrile diseases with similar symptoms.

Although the description of the embodiment of the present disclosure have been detailed described, the described embodiments are to be considered in all respects only as illustrative and not restrictive. It would be appreciated by those skilled in the art, modifications and alternatives can be made with those details, these changes are all within the scope of the present disclosure. The whole scope of the present disclosure is provided by attached claims and any equivalents thereof.

What is claimed is:

1. A method for rapidly diagnosing kawasaki disease, comprising quantitatively detecting miR-1246, miR-4436b-5p, miR-197-3p and miR-671-5p in serum exosomes, wherein the quantitative detection of miR-1246, miR-4436b-5p, miR-197-3p and miR-671-5p in serum exosomes comprises using primers as set forth in SEQ ID NOs: 9-16 for the detection of miR-1246, miR-4436b-5p, miR-197-3p and miR-671-5p by fluorescence-based quantitative PCR.

2. A kit for rapid diagnosis of kawasaki disease, comprising primers as set forth in SEQ ID NOs: 9-16 for the detection of miR-1246, miR-4436b-5p, miR-197-3p and miR-671-5p by fluorescence-based quantitative PCR.

3. The kit for rapid diagnosis of kawasaki disease according to claim 2, characterized in that the kit further comprises primers as set forth in SEQ ID NOs: 5-8 for reverse transcription of miR-1246, miR-4436b-5p, miR-197-3p and miR-671-5p.

* * * * *